US007015179B1

(12) United States Patent
Massaro et al.

(10) Patent No.: US 7,015,179 B1
(45) Date of Patent: Mar. 21, 2006

(54) REDUCED ODOR TOILET BAR COMPOSITION

(75) Inventors: Michael Massaro, Monroe, CT (US); Sandra Dawn Meraviglia, Milford, CT (US); Syed Husain Abbas, Seymour, CT (US); Bipinchandra J. Khara, West Windsor, NJ (US); Makarand S Shevade, Plainsboro, NJ (US); Michael Bernardus Van Vlijmem, Plainsboro, NJ (US)

(73) Assignee: Unilever Home & Personal Care USA, Greenwich, CT (US)

( * ) Notice: Subject to any disclaimer, the term of this patent is extended or adjusted under 35 U.S.C. 154(b) by 157 days.

(21) Appl. No.: 11/019,794

(22) Filed: Dec. 22, 2004

(51) Int. Cl.
*A61K 7/50* (2006.01)

(52) U.S. Cl. ...................... 510/101; 510/141; 510/152; 510/153; 510/155; 510/447

(58) Field of Classification Search ................ 510/101, 510/141, 152, 153, 155, 447
See application file for complete search history.

(56) References Cited

U.S. PATENT DOCUMENTS

| | | | |
|---|---|---|---|
| 4,169,900 A | 10/1979 | Mussinan et al. | |
| 5,518,665 A | 5/1996 | Kaneko et al. | |
| 5,560,906 A | 10/1996 | Scodari et al. | |
| 6,204,229 B1 | 3/2001 | Hasegawa et al. | |
| 6,610,648 B1 | 8/2003 | McGee et al. | |
| 6,630,438 B1 * | 10/2003 | Arnau et al. ................ | 510/439 |
| 6,723,687 B1 | 4/2004 | Clare | |

OTHER PUBLICATIONS

JP 2003055180 (Hideaki, et al.) *Abstract*.

* cited by examiner

*Primary Examiner*—Necholus Ogden
(74) *Attorney, Agent, or Firm*—Alan A. Bornstein

(57) ABSTRACT

Toilet bar compositions are described that contain specific odor masking agent(s). The odor masking agent(s) reduce malodor without the need for elevated amounts of masking fragrances that individuals may not prefer and who use the composition for personal cleansing or who are exposed to the composition.

8 Claims, No Drawings

REDUCED ODOR TOILET BAR COMPOSITION

BACKGROUND OF THE INVENTION

1. Field of the Invention

This invention relates generally to toilet bar compositions, and more particularly to specific toilet bar compositions having reduced malodor or base odor with reduced amounts of added fragrance or having no fragrance added.

2. The Related Art

Malodor is a common problem perceived in toilet bar. The underlying cause of the malodor is perceived to be from the formulation ingredients. It may also be due to the interaction of the ingredients used in the product. Malodor has a very negative impact on consumers, and becomes worse when the product comes in direct contact with skin. The malodor normally is masked by fragrance added to the product. Some consumers choose to avoid products that contain fragrance or essential oils for various reasons. It therefore becomes a challenge to cover the base odor or malodor in the product when fragrance is not desirable at the levels needed to act as an effective odor-masking agent. To overcome this problem, a composition and method for its production was surprisingly discovered. In this composition, Maltol, ethyl maltol or their analogues, derivatives or blends thereof, are used at effective levels in order to eliminate or substantially reduce the malodor or base odor of specific toilet bar compositions.

Maltol, ethyl maltol and selected analogues and their derivatives have found use as a perfume ingredient in various cleansing compositions. In U.S. Pat. No. 6,723,687 titled "Automatic Dishwashing Compositions Comprising Diacyl Peroxide Bleach and Blooming Perfume"; U.S. Pat. No. 5,518,665 titled "Transparent Solid Detergents" and U.S. Pat. No. 6,204,229 titled "Composition to be Applied to Hair or Skin; the use of maltol or ethyl maltol as a masking ingredient or perfume in various detergent compositions is disclosed.

SUMMARY OF THE INVENTION

In one aspect of the invention is a toilet bar, including but not limited to the following:

(a) fatty acid soap(s) in the total concentration range of about 5 to 75% by wt.; (b) free C6 to C22 carboxylic acid(s) in the total concentration range of about 4 to 40% by wt.; (c) non-soap synthetic detergent(s) in the total concentration range of about 2 to 60% by wt.; (d) a maximum of about 20% by wt. of water; and (e) an effective concentration of pyran type odor masking agent(s) having the structure of I, II or a blend thereof

I

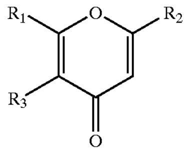

-continued

II

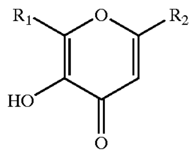

to reduce perceptible malodor in the toilet bar composition wherein R1 and R2 can be the same or different and are either hydrogen, alkyl, alkoxyl, alkenyl, alkylaryl, aryl or alkynyl, optionally substituted, and R3 is alkyl ester or alkenyl ester.

In another aspect of the invention is a process for manufacturing a reduced odor toilet bar including but not limited to the steps of where steps a to c are in no particular sequence:

a) blending one or more nonsoap anionic surfactants optionally with soap to form a detergent blend;

b) dispersing or dissolving pyran type odor masking agent(s) having the structure of I or II or a blend thereof in a sufficient amount of one or more polyol(s) to form an odor masking preblend to reduce perceptable malodor in the toilet bar,

I

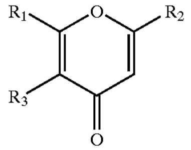

II

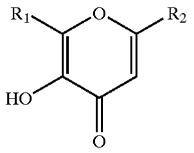

where R1 and R2 can be the same or different and are either hydrogen, alkyl, alkoxyl, alkenyl, alkylaryl, aryl or alkynyl, optionally substituted and R3 is alkyl ester or alkenyl ester;

c) adding the odor masking preblend to the detergent blend and mixing until homogenous to form a final blend; and finally d) extruding the final blend followed by cutting and stamping to form reduced odor toilet bars.

DETAILED DESCRIPTION OF THE INVENTION

In one aspect of the invention is a toilet bar, including but not limited to the following:

(a) fatty acid soap(s) in the total concentration range of about 5 to 75% by wt.; (b) free C6 to C22 carboxylic acid(s) in the total concentration range of about 4 to 40% by wt.; (preferably where the carboxylic acid(s) are C6 to C18 or C12 to C18 carboxylic acid(s)): (c) non-soap synthetic detergent(s) in the total concentration range of about 2 to 60% by wt.; (d) a maximum of about 20% by wt. of water; (preferably a maximum of about 15, 12, 10, 8, 6, 4 or 3% by wt. of water); and (e)

an effective concentration of pyran type odor masking agent(s) having the structure of I, II or a blend thereof

I

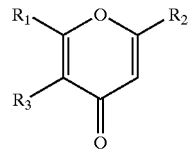

II

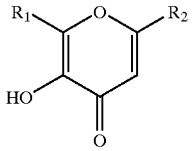

to reduce perceptible malodor in the toilet bar composition wherein R1 and R2 can be the same or different and are either hydrogen, alkyl, alkoxyl, alkenyl, alkylaryl, aryl or alkynyl, optionally substituted (preferably R1 and R2 are either hydrogen, C1 to C6 alkyl, C1 to C6 alkenyl, C1 to C6 alkoxyl, benzyl or phenyl and more preferably R1 is methyl or ethyl, and R2 is hydrogen) and R3 is alkyl ester or alkenyl ester (preferably C1–C5 alkyl or alkenyl ester).

Advantageously, the inventive toilet bar has a yield stress in the range of about 20 Kpa to 400 KPa at 25° C. and 50% RH measured as described below.

Preferably, the odor masking agent(s) is/are in the total concentration range of about 0.0005 to 0.25% by wt. (preferably with a minimum value of about 0.0025 or 0.004 and a maximum value of about 0.025, 0.01, 0.005 or 0.025). More preferably the inventive toilet bar further includes one or more polyol(s) in a total concentration range of about 0.01 to 30% by wt. (preferably with a minimum value of about 0.4 or 0.7 and a maximum value of about 2, 3, 7 or 10% by wt.). Most preferably these polyol(s) is/are selected from dipropylene glycol, propylene glycol, glycerin, or polyethylene glycol(s) in the MW range of about 200 to 1500 or blends thereof. Advantageously the polyol(s) have a viscosity under about 1000 cps at 30 C.

Advantageously the non-soap anionic surfactant(s) is/are selected from C8 to C14 acyl isethionates; C8 to C14 alkyl sulfates, C8 to C14 alkyl sulfosuccinates, C8 to C14 alkyl sulfonates; C8 to C14 fatty acid ester sulfonates, derivatives, or blends thereof. In a preferred embodiment, the odor masking agent is maltol (FIG. A), ethyl maltol (FIG. B) or a blend thereof.

In another aspect of the invention is a process for manufacturing a reduced odor toilet bar including but not limited to the steps of where steps a to c are in no particular sequence:

a) blending one or more nonsoap anionic surfactants optionally with soap to form a detergent blend;

b) dispersing or dissolving pyran type odor masking agent(s) having the structure of I or II or a blend thereof in a sufficient amount of one or more polyol(s) to form an odor masking preblend to reduce perceptable malodor in the toilet bar,

I

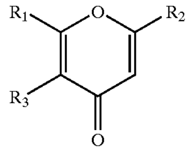

II

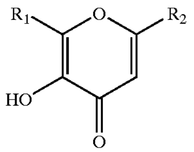

where R1 and R2 can be the same or different and are either hydrogen, alkyl, alkoxyl, alkenyl, alkylaryl, aryl or alkynyl, optionally substituted and R3 is alkyl ester or alkenyl ester;

c) adding the odor masking preblend to the detergent blend and mixing until homogenous to form a final blend; and finally d) extruding the final blend followed by cutting and stamping to form reduced odor toilet bars.

Surfactants:

Surfactants, also known as detergents, are an essential component of the inventive toilet bar composition. They are compounds that have hydrophobic and hydrophilic portions that act to reduce the surface tension of the aqueous solutions they are dissolved in. Useful surfactants include soap(s), and non-soap anionic, nonionic, amphoteric, and cationic surfactant(s), and blends thereof.

Anionic Surfactants:

The inventive toilet bar composition contains one or more non-soap anionic detergent(s) (syndets). Preferably the syndet(s) have a zein value of 50 or less. Zein value may be measured using the test method described below. Advantageously such non-soap anionic detergent(s) or surfactant(s) may be used in one preferred embodiment in the range of about 35 to 40% by wt. or in another preferred embodiment in a total concentration range of about 45 to 55% by wt. or a further preferred embodiment in a total concentration range of about 2 to 20% by wt. Anionic surfactants may advantageously constitute about 50, 60, 70, 80, 90 or 95% by wt. or more, of these amounts.

The anionic detergent active which may be used may be aliphatic sulfonate(s), such as a primary alkane (e.g., $C_8$–$C_{22}$) sulfonate(s), primary alkane (e.g., $C_8$–$C_{22}$) disulfonate(s), $C_8$–$C_{22}$ alkene sulfonate(s), $C_8$–$C_{22}$ hydroxyalkane sulfonate(s) or alkyl glyceryl ether sulfonate(s) (AGS); or aromatic sulfonate(s) such as alkyl benzene sulfonate.

The anionic may also be alkyl sulfate(s) (e.g., $C_{12}$–$C_{18}$ alkyl sulfate) or alkyl ether sulfate (including alkyl glyceryl ether sulfates). Among the alkyl ether sulfate(s) are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinate(s) (including mono- and dialkyl, e.g., $C_6$–$C_{22}$ sulfosuccinate(s)); alkyl and acyl taurate(s), alkyl and acyl sarcosinate(s), sulfoacetate(s), $C_8$–$C_{22}$ alkyl phosphate(s) and phosphate(s), alkyl phosphate ester(s) and alkoxyl alkyl phosphate ester(s), acyl lactate(s), $C_8$–$C_{22}$ monoalkyl succinate(s) and maleate(s), sulphoacetate(s), and alkyl glucoside(s) and the like.

Sulfosuccinates may be monoalkyl sulfosuccinates having the formula:

$R^4O_2CCH_2CH(SO_3M)CO_2M$; and amide-MEA sulfosuccinates of the formula;

$R^4CONHCH_2CH_2O_2CCH_2CH(SO_3M)CO_2M$ wherein $R^4$ ranges from $C_8$–$C_{22}$ alkyl and M is a solubilizing cation.

Sarcosinates are generally indicated by the formula:

$R^1CON(CH_3)CH_2CO_2M$, wherein $R^1$ ranges from $C_8$–$C_{20}$ alkyl and M is a solubilizing cation.

Taurates are generally identified by formula:

$R^2CONR^3CH_2CH_2SO_3M$ wherein $R^2$ ranges from $C_8$–$C_{20}$ alkyl, $R^3$ may be H or $C_1$–$C_4$ alkyl and M is a solubilizing cation.

Monoacyl and/or diacyl C8–C18 isethionate surfactants having the general formula:

$R\ C—O(O)—CH_2—CH_2—SO_3\ M^+$ or $(R\ C—O(O)—CH_2—CH_2—SO_3)_2\ M^{++}$ wherein R is an alkyl group having 8 to 18 carbons, and M is a mono or divalent cation such as, for example, sodium, potassium, ammonium, calcium and magnesium or other mono and divalent cations may be used. Preferably the isethionates have an average iodine value of less than 20.

Fatty Acid Soap

The inventive toilet bar composition includes soap. The term “soap” is used here in its popular sense, i.e., the alkali metal or alkanol ammonium salts of aliphatic alkane- or alkene monocarboxylic acids preferably having about 6 to 22 carbon atoms, more preferably about 6 to about 18 or about 12 to 18 carbon atoms. They may be further described as alkali metal carboxylates of aliphatic hydrocarbons. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be potassium soaps. The soaps may contain unsaturation in accordance with commercially acceptable standards. Excessive unsaturation is normally avoided to minimize color and odor issues. Advantageously such soap(s) may be used in one preferred embodiment in the range of about 15 to 25% by wt. or in another preferred embodiment in a total concentration range of about 7 to 10% by wt. or a further preferred embodiment in a total concentration range of about 60 to 70% by wt.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

Pyran Odor Masking Agents:

Specific examples of useful pyran type odor masking agents for the inventive toilet bar preferably include compounds with the structures described above, and the following specific compounds with the structures below and the like:

FIGS. A & B

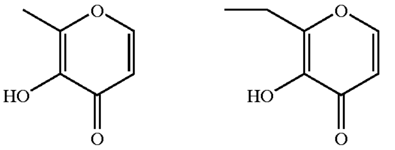

FIGS. C & D

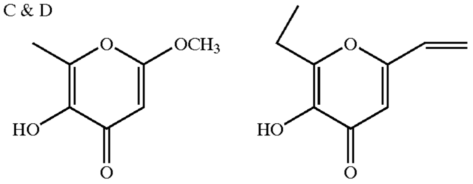

FIGS. E & F

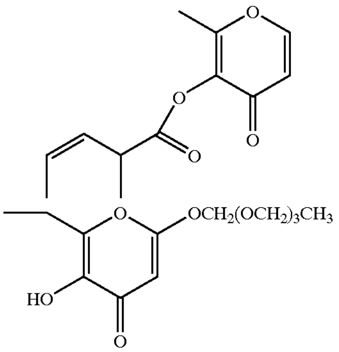

Amphoteric Surfactants

One or more amphoteric surfactants may be used in this invention. Amphoteric surfactants may be used from about 1, 2 or 3% by wt. to about 5, 6 or 7% by wt. when necessary.

Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$R^1—[—C(O)—NH(CH_2)_n—]_m—N^+—(R^2)(R^3)X—Y$ where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $—CO_2—$ or $—SO_3—$

Suitable amphoteric surfactants within the above general formula include simple betaines of formula:

$R^1—N^+—(R^2)(R^3)CH_2CO_2^-$ and amido betaines of formula:

$R^1—CONH(CH_2)_n—N^+—(R^2)(R^3)CH_2CO_2^-$ where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

$R^1—N^+-(R^2)(R^3)(CH_2)_3SO_3^-$ or $R^1—CONH(CH_2)_m—N^+—(R^2)(R^3)(CH_2)_3SO_3^-$ where m is 2 or 3, or variants of these in which $—(CH_2)_3SO_3^-$ is replaced by $—CH_2C(OH)(H)CH_2SO_3^-$ In these formulae $R^1$, $R^2$ and $R^3$ are as discussed previously.

Amphoacetates and diamphoacetates are also intended to be covered in the zwitterionic and/or amphoteric compounds which are used such as e.g., sodium lauroamphoacetate, sodium cocoamphoacetate, and blends thereof, and the like.

Nonionic Surfactants

One or more nonionic surfactants may also be used in the toilet bar composition of the present invention. When present, nonionic surfactants may be used at levels as low as about 1, 2 or 3% by wt. and as high as about 10, 15 or 20% by wt. in the inventive toilet bars.

The nonionics which may be used include in particularly the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Cationic Skin Conditioning Agents

An optional component in compositions according to the invention is a cationic skin feel agent or polymer, such as for example cationic celluloses or polyquarterium compounds.

Advantageously cationic skin feel agent(s) or polymer(s) are used from about 0.01, 0.1 or 0.2% by wt. to about 1, 1.5 or 2.0% by wt. in the inventive toilet bars.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200, and quaternary ammonium compounds such as alkyldimethylammonium halogenides.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Particularly preferred cationic polymers are JAGUAR C13S, JAGUAR C15, JAGUAR C17 and JAGUAR C16 and JAGUAR C162, especially Jaguar C13S. Other cationic skin feel agents known in the art may be used provided that they are compatible with the inventive formulation.

Other preferred cationic compounds that are useful in the present invention include amido quaternary ammonium compounds such as quaternary ammonium propionate and lactate salts, and quaternary ammonium hydrolyzates of silk or wheat protein, and the like. Many of these compounds can be obtained as the Mackine™ Amido Functional Amines, Mackalene™ Amido functional Tertiary Amine Salts, and Mackpro® cationic protein hydrolysates from the McIntyre Group Ltd. (University Park, Ill.).

In a preferred skin cleansing embodiment of the invention having a hydrolyzed protein conditioning agent, the average molecular weight of the hydrolyzed protein is preferably about 2500. Preferably 90% of the hydrolyzed protein is between a molecular weight of about 1500 to about 3500. In a preferred embodiment, MACKPRO™ WWP (i.e. wheat germ amido dimethylamine hydrolyzed wheat protein) is added at a concentration of 0.1% (as is) in the bar. This results in a MACKPRO™ WWP "solids" of 0.035% in the final bar formula for this embodiment.

Cationic Surfactants

One or more cationic surfactants may also be used in the inventive toilet bar composition. When desired, cationic surfactants may be used from about 0.1, 0.5 or 1.0% by wt. to about 1.5, 2.0 or 2.5% by wt.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol. I & II) by Schwartz, Perry & Berch, both of which are also incorporated into the subject application by reference.

In addition, the toilet bar composition of the invention may include 0 to about 15% by wt. optional ingredients as follows: sequestering agents, such as tetrasodium ethylenediaminetetraacetate (EDTA), EHDP or mixtures in an amount of about 0.01 to 1%, preferably about 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product. Perfumes may be included at levels of less than about 2, 1, 0.5 or preferably less than about 0.3, 0.2 or 0.1% by wt.

The compositions may further comprise preservatives such as dimethyloldimethylhydantoin (Glydant XL1000), parabens, sorbic acid etc., and the like. The compositions may also comprise coconut acyl mono- or diethanol amides as suds boosters, and strongly ionizing salts such as sodium chloride and sodium sulfate may also be used to advantage. Antioxidants such as, for example, butylated hydroxytoluene (BHT) and the like may be used advantageously in amounts of about 0.01% or higher if appropriate.

Skin conditioning agents such as emollients are advantageously used in the present invention for personal toilet bar compositions. Hydrophilic emollients including humectants such as polyhydric alcohols, e.g. glycerin and propylene glycol, and the like; polyols such as the polyethylene glycols listed below, and the like and hydrophilic plant extracts may be used. Advantageously humectants may be used from about 0.01, 0.2 or 1.0% by wt. to about 3, 5 or 10% by wt. in a toilet bar. Humectants may also confer the ability for the bar to retain water.

Polyox WSR-205 PEG 14M,
Polyox WSR-N-60K PEG 45M, or
Polyox WSR-N-750 PEG 7M.

Hydrophobic emollients may be used in the inventive toilet bar. Advantageously hydrophobic emollients may be used from about 5, 10 or 15% by wt. to about 20, 25, 30, 35, 40, 45% by wt. in the inventive toilet bar.

The term "emollient" is defined as a substance which softens or improves the elasticity, appearance, and youthfulness of the skin (stratum corneum) by increasing its water content, and keeps it soft by retarding the decrease of its water content.

Useful hydrophobic emollients include the following:

(a) silicone oils and modifications thereof such as linear and cyclic polydimethylsiloxanes; amino, alkyl, alkylaryl, and aryl silicone oils;

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic plant extracts;

(e) hydrocarbons such as liquid paraffin, petrolatum, microcrystalline wax, ceresin, squalene, pristan and mineral oil;

(f) higher fatty acids such as lauric, myristic, palmitic, stearic, behenic, oleic, linoleic, linolenic, lanolic, isostearic, arachidonic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils and extracts thereof such as *mentha*, jasmine, camphor, white cedar, bitter orange peel, ryu, turpentine, cinnamon, bergamot, *citrus unshiu*, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, *calendula*, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils; and (j) mixtures of any of the foregoing components, and the like.

Preferred hydrophobic emollient moisturizing agents are selected from fatty acids, di and triglyceride oils, mineral oils, petrolatum, silicone oils, and mixtures thereof; with fatty acids being most preferred for the toilet bar. Advantageously such fatty acids may be used in one preferred embodiment in the range of about 25 to 30% by wt. or in another preferred embodiment in a total concentration range of about 20 to 25% by wt. or in a further preferred embodiment in a total concentration range of about 2 to 10% by wt.

Krafft point

The Krafft point of a surfactant is defined as the temperature (or more precisely, the narrow temperature range) above which the solubility of a surfactant rises sharply. At this temperature the solubility of the surfactant becomes equal to the critical micelle concentration. It may be determined by locating the abrupt change in slope of a graph of the logarithm of the solubility against temperature or 1/T or can be rapidly estimated using the rapid estimation procedure described below.

Exfoliants

The inventive toilet bar may contain particles that are greater than 50 microns in average diameter that help remove dry skin. Not being bound by theory, the degree of exfoliation depends on the size and morphology of the particles. Large and rough particles are usually very harsh and irritating. Very small particles may not serve as effective exfoliants. Such exfoliants used in the art include natural minerals such as silica, talc, calcite, pumice, tricalcium phosphate; seeds such as rice, apricot seeds, etc; crushed shells such as almond and walnut shells; oatmeal; polymers such as polyethylene and polypropylene beads, flower petals and leaves; microcrystalline wax beads; jojoba ester beads, and the like. These exfoliants come in a variety of particle sizes and morphology ranging from micron sized to a few mm. They also have a range of hardness. Some examples are given in table A below.

TABLE A

| Material | Hardness (Mohs) |
|---|---|
| Talc | 1 |
| Calcite | 3 |
| Pumice | 4–6 |
| Walnut Shells | 3–4 |
| Dolomite | 4 |
| Polyethylene | ~1 |

Optional Active Agents

Advantageously, active agents other than skin conditioning agents defined above may be added to the inventive toilet bar. These active ingredients may be advantageously selected from bactericides, vitamins, anti-acne actives; antiwrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; or mixtures thereof; and the like.

These active agents may be selected from water-soluble active agents, oil soluble active agents, pharmaceutically acceptable salts and mixtures thereof. The term "active agent" as used herein, means personal care actives which can be used to deliver a benefit to the skin and/or hair and which generally are not used to confer a skin conditioning benefit, such are delivered by emollients as defined above. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent(s) will vary with the specific active agent, the ability of the active to penetrate through the skin, the age, health condition, and skin condition of the user, and other like factors. Preferably the personal toilet bar compositions of the present invention comprise from about 0.0001% to 50%, more preferably from about 0.05% to 25%, even more preferably about 0.1% to 10%, and most preferably about 0.1% % to 5%, by weight of the active agent component(s).

A wide variety of active agent ingredients are useful for the inventive personal toilet bar compositions and include those selected from anti-acne actives, anti-wrinkle and anti-skin atrophy actives, skin barrier repair aids, cosmetic soothing aids, topical anesthetics, artificial tanning agents and accelerators, skin lightening actives, antimicrobial and antifungal actives, sunscreen actives, sebum stimulators, sebum inhibitors, anti-glycation actives and mixtures thereof and the like.

Anti-acne actives can be effective in treating acne vulgaris, a chronic disorder of the pilosebaceous follicles. Nonlimiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e.g., cis and trans); sulfur-containing D and L amino acids and their derivatives and salts, particularly their N-acetyl derivatives, mixtures thereof and the like.

Antimicrobial and antifungal actives can be effective to prevent the proliferation and growth of bacteria and fungi. Nonlimiting examples of antimicrobial and antifungal actives include b-lactam drugs, quinolone drugs, ciprofloxacin, norfloxacin, tetracycline, erythromycin, amikacin, 2,4,4'-trichloro-2'-hydroxy diphenyl ether, 3,4,4'-Trichlorocarbanilide (triclocarban), phenoxyethanol, 2,4,4'-Trichloro-2'-Hydroxy Diphenyl Ether (triclosan); and mixtures thereof and the like.

Anti-wrinkle, anti-skin atrophy and skin repair actives can be effective in replenishing or rejuvenating the epidermal layer. These actives generally provide these desirable skin care benefits by promoting or maintaining the natural process of desquamation. Nonlimiting examples of antiwrinkle and anti-skin atrophy actives include vitamins, minerals, and skin nutrients such as milk, vitamins A, E, and K; vitamin alkyl esters, including vitamin C alkyl esters; magnesium, calcium, copper, zinc and other metallic components; retinoic acid and its derivatives (e.g., cis and trans); retinal; retinol; retinyl esters such as retinyl acetate, retinyl palmitate, and retinyl propionate; vitamin B 3 compounds (such as niacinamide and nicotinic acid), alpha hydroxy acids, beta hydroxy acids, e.g. salicylic acid and derivatives thereof (such as 5-octanoyl salicylic acid, heptyloxy 4 salicylic acid, and 4-methoxy salicylic acid); mixtures thereof and the like.

Skin barrier repair actives are those skin care actives which can help repair and replenish the natural moisture barrier function of the epidermis. Nonlimiting examples of skin barrier repair actives include lipids such as cholesterol, ceramides, sucrose esters and pseudo-ceramides as described in European Patent Specification No. 556,957; ascorbic acid; biotin; biotin esters; phospholipids, mixtures thereof, and the like.

Non-steroidal Cosmetic Soothing Actives can be effective in preventing or treating inflammation of the skin. The soothing active enhances the skin appearance benefits of the present invention, e.g., such agents contribute to a more uniform and acceptable skin tone or color. Nonlimiting examples of cosmetic soothing agents include the following categories: propionic acid derivatives; acetic acid derivatives; fenamic acid derivatives; mixtures thereof and the like. Many of these cosmetic soothing actives are described in U.S. Pat. No. 4,985,459 to Sunshine et al., issued Jan. 15, 1991, incorporated by reference herein in its entirety.

Artificial tanning actives can help in simulating a natural suntan by increasing melanin in the skin or by producing the appearance of increased melanin in the skin. Nonlimiting examples of artificial tanning agents and accelerators include dihydroxyacetaone; tyrosine; tyrosine esters such as ethyl tyrosinate and glucose tyrosinate; mixtures thereof, and the like.

Skin lightening actives can actually decrease the amount of melanin in the skin or provide such an effect by other mechanisms. Nonlimiting examples of skin lightening actives useful herein include aloe extract, alpha-glyceryl-L-ascorbic acid, aminotyrosine, ammonium lactate, glycolic acid, hydroquinone, 4 hydroxyanisole, mixtures thereof, and the like.

Also useful for the inventive personal toilet bar compositions are sunscreen actives. A wide variety of sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Nonlimiting examples of sunscreens which are useful in the compositions of the present invention are those selected from the group consisting of octyl methoxyl cinnamate (Parsol MCX) and butyl methoxy benzoylmethane (Parsol 1789), 2-ethylhexyl p-methoxycinnamate, 2-ethylhexyl N,N-dimethyl-p-aminobenzoate, p-aminobenzoic acid, 2-phenylbenzimidazole-5sulfonic acid, oxybenzone, mixtures thereof, and the like.

Sebum stimulators can increase the production of sebum by the sebaceous glands. Nonlimiting examples of sebum stimulating actives include bryonolic acid, dehydroetiandrosterone (DHEA), orizanol, mixtures thereof, and the like.

Sebum inhibitors can decrease the production of sebum by the sebaceous glands. Nonlimiting examples of useful sebum inhibiting actives include aluminum hydroxy chloride, corticosteroids, dehydroacetic acid and its salts, dichlorophenyl imidazoldioxolan (available from Elubiol), mixtures thereof, and the like.

Also useful as actives in the inventive personal toilet bar compositions are protease inhibitors. Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the inventive personal toilet bar compositions include, but are not limited to, proteinases such as serine proteases, metalloproteases, cysteine proteases, and aspartyl protease, and peptidases, such as carboxypepidases, dipeptidases and aminopepidases, mixtures thereof and the like.

Other useful active ingredients in the inventive personal toilet bar compositions are skin tightening agents. Nonlimiting examples of skin tightening agents which are useful in the compositions of the present invention include monomers which can bind a polymer to the skin such as terpolymers of vinylpyrrolidone, (meth)acrylic acid and a hydrophobic monomer comprised of long chain alkyl (meth)acrylates, mixtures thereof, and the like.

Active ingredients in the inventive personal toilet bar compositions may also include anti-itch ingredients. Suitable examples of anti-itch ingredients which are useful in the compositions of the present invention include hydrocortisone, methdilizine and trimeprazine, mixtures thereof, and the like.

Nonlimiting examples of hair growth inhibitors which are useful in the inventive personal toilet bar compositions include 17 beta estradiol, anti angiogenic steroids, *curcuma* extract, cycloxygenase inhibitors, evening primrose oil, linoleic acid and the like. Suitable 5-alpha reductase inhibitors such as ethynylestradiol and, genistine mixtures thereof, and the like.

Nonlimiting examples of desquamating enzyme enhancers which are useful in the inventive personal toilet bar compositions include alanine, aspartic acid, N methyl serine, serine, trimethyl glycine, mixtures thereof, and the like.

A nonlimiting example of an anti-glycation agent which is useful in the compositions of the present invention would be Amadorine (available from Barnet Products Distributor), and the like.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated. Physical test methods are described below. The following inventive toilet bar compositions may be formulated according to the manufacturing methods described below:

Example 1

Useful synthetic detergent toilet bars according to the present invention (Inv.) as compared to a comparative bar (Comp.) can be prepared according to table 1:

TABLE 1

| Ingredients | A (Comp.) | B (Inv.) | C (Inv.) | D (Inv.) |
|---|---|---|---|---|
| Sodium cocyl isethionate | 50.00 | 50.00 | 50.00 | 50.00 |
| Sodium Isethionate | 10.00 | 10.00 | 10.00 | 10.00 |
| Stearic acid | 23.00 | 23.40 | 23.20 | 23.00 |
| Coco betaine | 3.00 | 3.00 | 3.00 | 3.00 |
| 82/18 tallow/coco Soap | 4.00 | 4.00 | 4.00 | 4.00 |

TABLE 1-continued

| Ingredients | A (Comp.) | B (Inv.) | C (Inv.) | D (Inv.) |
|---|---|---|---|---|
| Preservatives/Opacifiers | 0.50 | 0.50 | 0.50 | 0.50 |
| Sodium Stearate | 1.50 | 1.50 | 1.50 | 1.50 |
| Coconut fatty acid | 2.00 | 2.00 | 2.00 | 2.00 |
| Ethyl maltol or maltol | | 0.003 | 0.004 | 0.01 |
| Polyol (e.g. Dipropylene glycol (DPG)) | | 0.597 | 0.796 | 0.99 |
| Perfume | 1.00 | | | |
| Water | 5.00 | 5.00 | 5.00 | 5.00 |
| Total | 100.00 | 100.00 | 100.00 | 100.00 |

Example 2

Useful combination toilet bars according to the present invention (Inv.) as compared to a comparative bar (Comp.) can be prepared according to table 2:

TABLE 2

| Ingredients | E (Comp.) | F (Inv.) | G (Inv.) | H (Inv.) |
|---|---|---|---|---|
| 70/30 tallow/coco Soap base | 76.46 | 74.45 | 63.960 | 68.700 |
| Sodium cocoyl isethionate | | | 20.000 | 10.000 |
| Stearic acid | 5.00 | 5.00 | 4.000 | 5.000 |
| Alpha C10–14 olefin sulfonate | 3.00 | 3.00 | | 2.000 |
| Cocoamidopropyl betaine | 3.00 | 3.00 | | 2.000 |
| Preservatives/Opacifiers | 0.54 | 0.54 | 0.540 | 0.540 |
| Maltol | | 0.01 | 0.003 | 0.004 |
| Polyol (DPG) | | 2.00 | 0.497 | 0.756 |
| Petrolatum/Mineral Oil | 2 | 2 | 1 | 1 |
| Water | 10.00 | 10.00 | 10.000 | 10.000 |
| Total | 100.00 | 100.00 | 100.000 | 100.000 |

Example 3

Useful synthetic toilet bars with maltol and/or ethyl maltol and reduced fragrance level according to the present invention (Inv.) as compared to a comparative bar (Comp.) can be prepared according to table 3:

TABLE 3

| Ingredients | I (Comp.) | J (Inv.) | K (Inv.) | L (Inv.) |
|---|---|---|---|---|
| Sodium cocoyl isethionate | 50 | 50 | 49.5 | 49.2 |
| Sodium isethionate | 10 | 10 | 10 | 10 |
| Stearic acid | 23 | 23.4 | 23.4 | 23.4 |
| Coco betaine | 3 | 3 | 3 | 3 |
| 82/18 Soap (tallow/coco) | 4 | 4 | 4 | 4 |
| Preservatives/Opacifiers | 0.5 | 0.5 | 0.5 | 0.5 |
| Sodium stearate | 1.5 | 1.5 | 1.5 | 1.5 |
| Coconut fatty acid | 2 | 2 | 2 | 2 |
| Water | 5 | 5 | 5 | 5 |
| Ethyl maltol or maltol | | 0.003 | 0.003 | 0.003 |
| Dipropylene glycol | | 0.597 | 0.597 | 0.597 |
| Perfume | 1 | | 0.5 | 0.8 |
| Total | 100 | 100 | 100 | 100 |

Example 4

Useful synthetic toilet bars with maltol and/or ethyl maltol in place of some or all of the maltol and reduced fragrance level according to the present invention (Inv.) as compared to a comparative bar (Comp.) can be prepared according to table 4:

TABLE 4

| Ingredients | M (Comp.) | O (Inv.) | P (Inv.) | Q (Inv.) | R (Inv.) | S (Inv.) | T (Inv.) |
|---|---|---|---|---|---|---|---|
| Sodium Cocoyl Isethionate | 37.0 | 35.49 | 47.5 | 35.74 | 32.74 | 29.74 | 37.24 |
| Sodium C14–16 Olefin Sulfonate | 3.0 | 3.0 | — | 3.0 | — | 3.0 | 3.0 |
| Cocamidopropyl Betaine | — | — | 3.0 | — | — | — | — |
| Starch | — | — | — | — | 5.0 | — | — |
| Kaolin | — | — | — | — | — | 5.0 | — |
| Calcium Sulfate | — | — | — | 1.0 | — | — | — |
| Sodium Lauryl Sulfate | — | — | — | — | — | — | 2.5 |
| Coco Sulfosuccinate | — | — | — | — | 5.0 | — | — |
| Coconut Acid | 5.0 | 5.0 | 6.0 | 5.0 | 4.0 | 5.0 | 5.0 |
| Stearic Acid | 19.75 | 20.0 | 16.0 | 20.0 | 16.0 | 20.0 | 15.0 |
| Sodium Stearate | 10.0 | 10.0 | 4.0 | 10.0 | 10.0 | 10.0 | 10.0 |
| Titanium Dioxide | 0.25 | 0.25 | 0.25 | 0.25 | 0.25 | 0.25 | 0.25 |
| Sodium Chloride | 0.5 | — | — | — | — | — | — |
| 82/18 Tallow/Coco Soap | 13.0 | 13.0 | 12.0 | 13.0 | 15.0 | 15.0 | 15.0 |
| Sodium Isethionate | 5.0 | 5.0 | 5.0 | 5.0 | 5.0 | 5.0 | 5.0 |
| Water | 5.5 | 6.0 | 5.5 | 6.0 | 6.0 | 6.0 | 6.0 |
| Maltol | | 0.01 | 0.003 | 0.004 | 0.004 | 0.004 | 0.004 |
| Polyol (DPG) | 0.75 | 2.00 | 0.497 | 0.756 | 0.756 | 0.756 | 0.756 |
| Preservatives | 0.25 | 0.25 | 0.25 | 0.25 | 0.25 | 0.25 | 0.25 |
| Total: | 100 | 100 | 100 | 100 | 100 | 100 | 100 |

Processing Method:

The bar can be formulated as follows:

In the syndet bar process, first melt the emollients and structurants by heating above 90 C in a z-blade mixer. Then add the anionic surfactants in the mixer and homogenize the mass to form the base. Other optional ingredients such as titanium dioxide, brighteners and clays can be added to the mixer at this time. The free water content of the mass is optimally adjusted to about 5–6%. The resulting doughy or flowable liquid mass is then chill roll milled. The milled mass is added in the chip mixer and the rest of the minor ingredients such as color, optional fragrance and specialty ingredients are added and mixed. Ethyl maltol is added at this point and mixed with the base. It has been observed that the pre-dilution of ethyl maltol (EM) in polyol(s) or perfume(s) provides better dispersion in the final product. Different types of polyols may be used to solubilize EM. Surprisingly it was observed that the color and the odor of the inventive toilet bar were more stable in dipropylene glycol (DPG) after aging for 4 weeks at 43° C. Another observation is that in the initial stage one can detect the characteristic odor of Maltol, which is described as a fruity candy-like odor, but on aging for a period of about 2–3 weeks this characteristic odor slowly disappears and the bar becomes nearly odorless provided that the bar does not contain added perfume. In the instant invention in a preferred embodiment, a premix is made separately with EM and the polyol; e.g. EM is mixed with DPG at 0.5% by wt. level. This pre-mix is added in the base at 0.1–2.0% level or more as desired in the chip-mixer. The mixed mass is then milled/refined and extruded. The extruded bars are stamped and cartoned/wrapped.

The combar toilet bars can be made by mixing the maltol blend with the base and other ingredients in the chip mixer. Then the mixed mass can be processed to get the final bar by the method mentioned above.

Cast Melt Bars.

Flowable and castable inventive compositions can be made using art recognized and other equivalent techniques. Suitable compositions may be made by adding low Krafft point surfactants/structurants/emollients/humectants/solvents,etc (preferably surfactant KP<30 C) and/or water in a total range of 10–30% by wt., preferably greater than 10%, 12%, 14, and 15% by wt. Very high levels are preferably avoided in order to minimize the mush factor of the cast melt toilet bar.

In a preferred embodiment, a mixture of sodium cocoyl isethionate, and magnesium cocoyl isethionate is structured by using an effective quantity of sodium stearate or 12 hydroxystearic acid in presence of emollients for skin conditioning such as e.g. glycerin, propylene glycol and/or fatty alcohols. These emollients act as solubilizers which are needed to obtain a homogeneous liquid at elevated temperature which on cooling yields a hard bar as determined by its yield stress. Optionally a quantity of cosurfactants with Krafft point preferably less than 30 C can also be used in the formulations.

Method of making the bars:

In addition to the inventive odor masking agent, optional fragrance, sunflower seed oil, SCI and $MgCl_2$, the remainder of the ingredients are added in a mixer. The mixture is heated to about 90C and mixed slowly to make a homogeneous liquid. SCI and $MgCl_2$ is added slowly and dissolved at about 100 C. Once the mass is homogeneous, the temperature is brought to about 80 C and sunflower seed oil is added slowly with continuous mixing. Fragrance is optionally added to the homogeneous mass preferably at about 70 C to avoid fragrance deterioration. This homogeneous off-white liquid is poured into molds. The molds are cooled by suitable cooling techniques or under ambient conditions to obtain solid bars.

Description of Test Methods

Test Methods

A) Analytical method for estimating the maltol, ethyl maltol or its derivatives and analogues content of a toilet bar.

Pyran type odor masking compounds such as maltol and ethyl maltol can be quantified using the following Solid Phase Micro Extraction (SPME) Headspace Sampling method applied to the toilet bar.

A CTC Analytics Pal automated SPME sampling system was used to sample the headspace of bar soap samples. The SPME fiber was then desorbed into a GC-MS. The following parameters were used:

Sample Preparation:
2 g sample into 20 ml headspace sampling vial
Vial was sealed with septum crimp cap SPME Headspace Sampling Parameters:
Equilibration time: 2 mins.
Sampling Time: 30 mins.
Sample temperature: 35° C.
SPME Fiber: DVB/CAR/PDMS (gray) Supelco (Belleton, Pa.) part # 57299-U SPME Fiber Desorption Parameters:
Inlet temp: 250° C.
Desorption time: 5 mins GC-MS Parameters:
Column: SPB-1 30 m×0.25 mm×0.25 um thickness (100% Methyl Silicone column obtained from Supelco (Belleton, Pa.).
Carrier gas: helium
Flow: 1 ml/min
Split mode: Splitless
Oven: 50° C. hold for 3 mins.
Ramp: 6° C./Min
Final temperature: 240 hold for 10 mins.
Total time: 45 mins
Detector: Agilent Mass Selective detector
Configuration: Scan 35–350

B) Method for calculation of yield stress with cheese cutter device

An approximate value for yield stress can be determined by the cheese cutter method. The principle of the measurement is that a wire penetrating into a material with a constant force will come to rest when the force on the wire due to stress balances the weight. The force balance is:

Weight driving wire=force on wire due to material stress m g=K ys I D where
m=mass driving wire (actual mass used in calculation is the mass placed on the device plus the weight of the arm which adds to the extra weight on the sample)
g=gravitational constant, 9.8 m/sec$^2$
ys=yield stress
I=length of penetration of wire into soap after 1 minute (mm)
D=diameter of wire (mm)
K=a geometrical constant The final equation is:

$$ys=(3/8)m\ g/(I\ D)$$

Procedure:

Cut a square of soap and position on the yield stress device. Place a mass on the yield stress device while holding the arm. 400 g is an appropriate mass, although less might be needed for a very soft material. Gently lower the arm so the wire just touches the soap and let the arm go. Stop the vertical motion of the arm after one minute, and push the soap through the wire horizontally to cut a wedge out of the sample. Take the mass off the device and then measure the length of the cut in the sample. The wire would continue to cut the soap at a slow rate, but the length of the cut made by the wire in one minute is taken as the final value. Measure the temperature of the soap while the test proceeds.

Sample calculation:

A 400 gram weight is used on the yield stress device and a 22 mm slice is measured where the wire has cut the soap after 1 minute. Assuming the diameter of the wire is 0.6 mm, the approximate yield stress is $$\frac{(3/8)(400+56)\ [\text{g}]\ \ 9.8\ [\text{m/sec}^2]\ 10^{-3}\ [\text{kg/g}]}{22\ [\text{mm}]\ 0.6\ [\text{mm}]\ 10^{-6}\ [\text{m}^2/\text{mm}^2]} = 1.3105\ \text{Pa or }\ 130\ \text{kPa}$$

Optionally an Instron testing device (supplied by Instron Co., Boston, Mass.) may be used instead of a weight to apply stress to the wire contacting the bar.

c) Krafft point determination

Make up a 10% by wt. solution of surfactant or other sample in water. If needed, heat the system to dissolve the sample completely. Transfer the clear solution to a glass test tube. Place the test tube in a beaker equipped with a stirrer and filled with sufficient water to evenly cool the surfactant or sample solution. The solution should be cooled with continuous stirring and the temperature should be continuously recorded. Note the temperature when the crystallization process begins such that the solution becomes turbid. This temperature is taken as the Krafft point. If the crystallization temperature is below room temperature, add ice to the beaker to cool the test tube below room temperature to measure the subambient Krafft point.

d) Zein test method

The inventive toilet bar composition (especially for personal cleansing of the skin and hair) preferably has a zein solubility of under about 50, 40, 30, and most preferably under about 25 using the zein solubility method set forth below. The lower the zein score, the milder the product is considered to be. This method involves measuring the solubility of zein (corn protein) in cleansing base solutions as follows:

0.3 g of cleansing base and 29.7 g of water at room temperature (25C).

are mixed thoroughly. To this is added 1.5 g of zein, and mixed for 1 hour. The mixture is then centrifuged for 30 minutes at 3000 rpm. After centrifugation, the pellet is extracted, washed with water, and dried in a vacuum oven for 24 hours until substantially all the water has evaporated. The weight of the dried pellet is measured and percent zein solubilized is calculated using the following equation:

% Zein solubilized=100 (1−weight of dried pellet/1.5).

The % Zein is further described in the following references: E. Gotte, Skin compatibility of tensides measured by their capacity for dissolving zein protein, Proc. IV International Congress of Surface Active Substances, Brussels, 1964, pp 83–90.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A toilet bar composition, comprising:

(a) fatty acid soap(s) in the total concentration range of about 5 to 75% by wt.;

(b) free C6 to C22 carboxylic acid(s) in the total concentration range of about 4 to 40% by wt.;

(c) non-soap synthetic detergent(s) in the total concentration range of about 2 to 60% by wt.;

(d) a maximum of about 20% by wt. of water; and (e) an effective concentration of pyran type odor masking agent(s) having the structure of I, II or a blend thereof

I

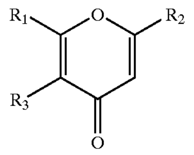

II

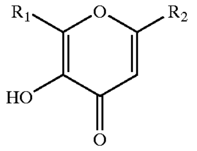

to reduce perceptible malodor in the toilet bar composition wherein R1 and R2 can be the same or different and are either hydrogen, alkyl, alkoxyl, alkenyl, alkylaryl, aryl or alkynyl, optionally substituted and R3 is alkyl ester or alkenyl ester.

2. The toilet bar composition of claim 1 which is in the form of a toilet bar having a yield stress in the range of about 20 Kpa to 400 KPa at 25° C. and 50% RH.

3. The toilet bar composition of claim 1 wherein the odor masking agent(s) is/are in the total concentration range of about 0.0005 to 0.25% by wt.

4. The toilet bar composition of claim 1 further comprising one or more polyol(s) in a total concentration range of about 0.01 to 30% by wt.

5. The toilet bar composition of claim 4 wherein the one or more polyol(s) is/are selected from dipropylene glycol, propylene glycol, glycerin, or polyethylene glycol(s) in the MW range of about 200 to 1500 or blends thereof.

6. The toilet bar composition of claim 1 wherein the non-soap anionic surfactant(s) is/are selected from C8 to C14 acyl isethionates; C8 to C14 alkyl sulfates, C8 to C14 alkyl sulfosuccinates, C8 to C14 alkyl sulfonates; C8 to C14 fatty acid ester sulfonates, derivatives, or blends thereof.

7. The toilet bar composition of claim 1 wherein the odor masking agent is maltol, ethyl maltol or a blend thereof.

8. A process for manufacturing a reduced odor toilet bar comprising the steps of where steps a to c are in no particular sequence:

a) blending one or more nonsoap anionic surfactants optionally with soap to form a detergent blend;

b) dispersing or dissolving pyran type odor masking agent(s) having the structure of I or II or a blend thereof in a sufficient amount of one or more polyol(s) to form an odor masking preblend to reduce perceptible malodor in the toilet bar,

I

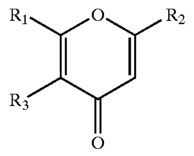

II

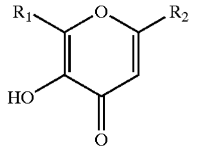

where R1 and R2 can be the same or different and are either hydrogen, alkyl, alkoxyl, alkenyl, alkylaryl, aryl or alkynyl, optionally substituted and R3 is alkyl ester or alkenyl ester;

c) adding the odor masking preblend to the detergent blend and mixing until homogenous to form a final blend; and finally d) extruding the final blend followed by cutting and stamping to form reduced odor toilet bars.

* * * * *